United States Patent [19]
Botich et al.

[11] Patent Number: 5,407,431
[45] Date of Patent: Apr. 18, 1995

[54] INTRAVENOUS CATHETER INSERTION DEVICE WITH RETRACTABLE NEEDLE

[75] Inventors: Michael J. Botich, Oxnard; Thor Halseth, Simi Valley, both of Calif.

[73] Assignee: Med-Design Inc., Ventura, Calif.

[21] Appl. No.: 127,962

[22] Filed: Sep. 27, 1993

Related U.S. Application Data

[63] Continuation-in-part of Ser. No. 17,832, Feb. 16, 1993, abandoned, which is a continuation of Ser. No. 656,305, Feb. 15, 1991, Pat. No. 5,188,599, Continuation-in-part of Ser. No. 378,275, Jul. 11, 1989, Pat. No. 4,994,034.

[51] Int. Cl.$^6$ .............................................. A61M 5/24
[52] U.S. Cl. ................................... 604/110; 604/164; 604/198
[58] Field of Search ............... 604/110, 192, 194, 195, 604/197, 198, 220, 226, 240, 164

[56] References Cited

U.S. PATENT DOCUMENTS

| | | | |
|---|---|---|---|
| 5,084,018 | 1/1992 | Tsao | 604/110 |
| 5,129,884 | 7/1992 | Dysarz | 604/164 |
| 5,180,369 | 1/1993 | Dysarz | 604/110 |
| 5,211,629 | 5/1993 | Pressly et al. | 604/110 |

*Primary Examiner*—Corrine Maglione
*Attorney, Agent, or Firm*—Cislo & Thomas

[57] ABSTRACT

A hypodermic injection system (7) with a retractable needle (9) wherein the needle (9) retracts within an interior cavity of a syringe plunger (59), such that the needle (9) is confinedly held within the plunger (59). A cylindrical spring housing assembly (21) has resilient fingers (23) which captures a spring (15) biasly holding a needle holder (11) against the retaining force of resilient fingers (23). The plunger (59) has a frangible end (65), which dissociates when the outwardly tapered shoulders (68) spread the resilient fingers (23), allowing the coiled spring (15) to eject the needle (9) and its holder (11) into the interior cavity (71) of the plunger (59). A body fluid sampling embodiment employs the same functional elements except the plunger (59") is shorter and contains a linking (137) that communicates with a vacuum container (147). The container allows fluid sampling and provides the structure to release the spring (15") retracting the needle (9"). The retractable needle embodiment is also employed with an insertion needle (9"') that guides a catheter tube (154) below the skin of a patient and into the vein, and allows retraction of the insertion needle (9"') thereby avoiding accidental pricking of the health care worker by the insertion needle (9"').

25 Claims, 8 Drawing Sheets

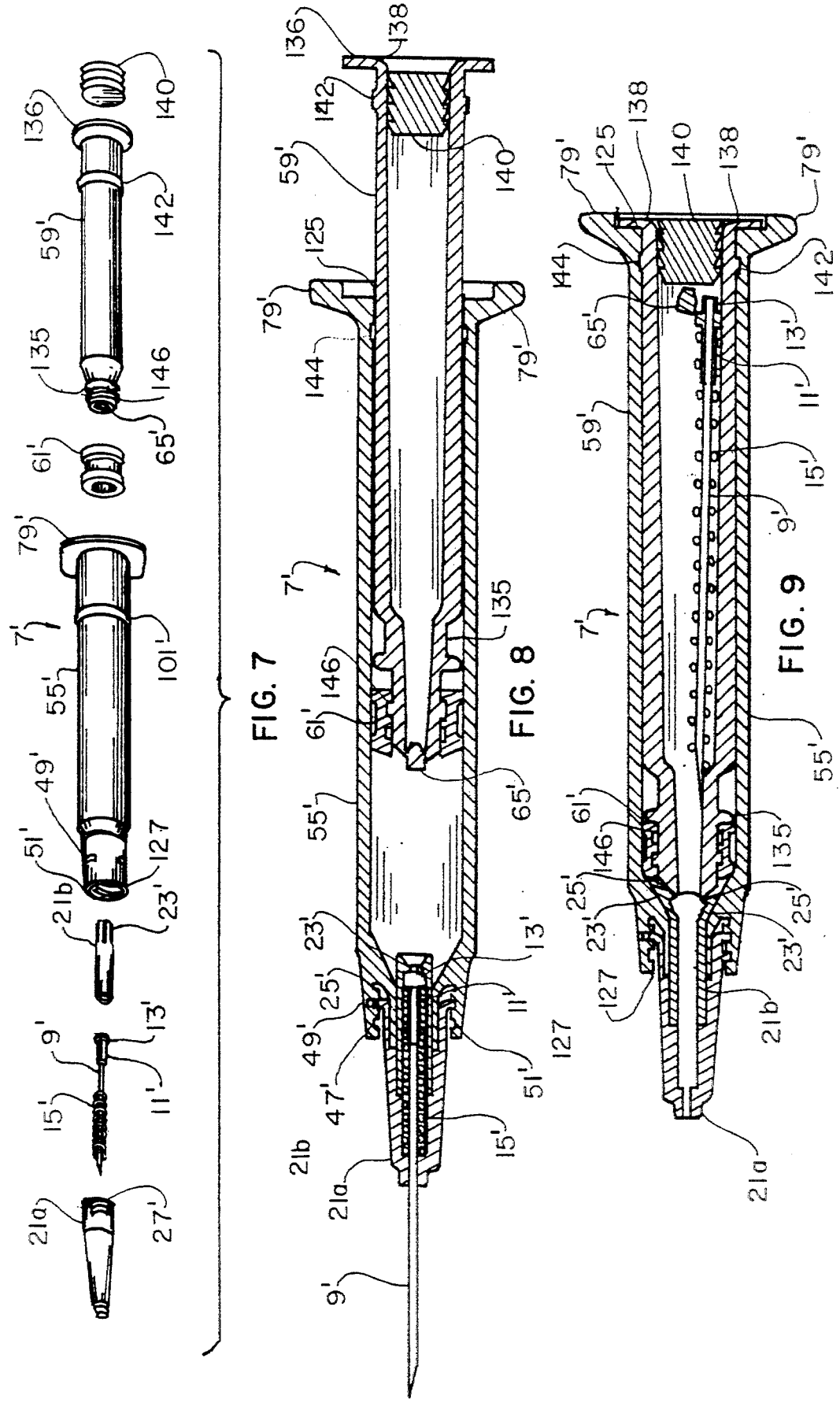

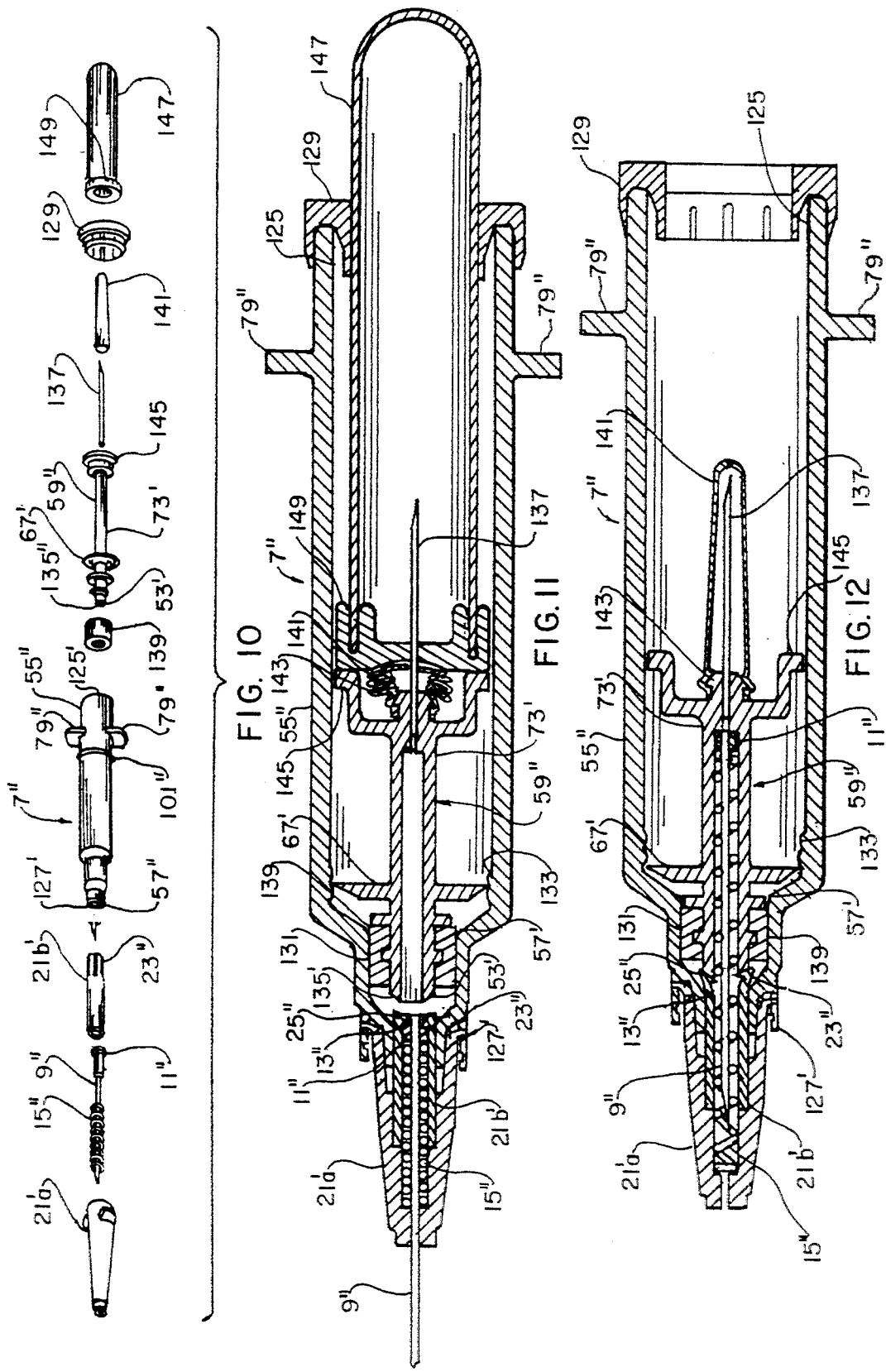

INTRAVENOUS CATHETER INSERTION DEVICE WITH RETRACTABLE NEEDLE

CROSS REFERENCE TO RELATED APPLICATION

This application is a Continuation In Part of application Ser. No. 08/017,832, filed Feb. 16, 1993, now abandoned, which is a Continuation of U.S. Pat. No. 5,188,599, originally filed as application Ser. No. 07/656,305, filed Feb. 15, 1991, which is a Continuation-In-Part of U.S. Pat. No. 4,994,034, originally filed as application Ser. No. 07/378,275, filed Jul. 11, 1989.

TECHNICAL FIELD

This invention relates generally to retractable needle systems and particularly to hypodermic syringes and intravenous catheter insertion devices that are suited for quickly and effectively removing the sharp insertion needle which poses a serious health threat.

BACKGROUND ART

Various types of retractable needle systems currently exist in the art, with the object being to provide a protective cover or cap over the possibly wound-inflicting insertion needle. Insertion needles found in intravenous catheter insertion devices and hypodermic syringes must be very sharp to quickly and easily puncture the skin and tissue of the patient in order to provide medication directly into the vascular system. Additionally, the insertion needle is usually very thin and hard to see, especially in low-light conditions. It is possible for doctors and nurses to accidentally prick themselves with the needle, either prior to or after an insertion into a patient.

Pricking oneself prior to the insertion of a solution does not present much of a health risk, since the needles to be used are normally sterilized. Also, the insertion needle usually comes with a needle cap which is secured over the top of the needle to prevent the accidental puncturing of skin. When the doctor or nurse removes the needle cap, exposing the needle, there is little risk of being injured by the needle. However, upon removal and placing the needle cap back onto the needle, the fingers can be pricked by a slight visual miscalculation or by a motorneuro mistake. The consequences of this type of accident are more extreme.

Since the insertion needle has already punctured the skin and tissue of the patient, blood and body fluid containing viruses or bacteria which may be found in the patient could possibly be transferred to the health care provider by a single accidental prick.

Various types of diseases previously known could be conveyed by such an accident, including hepatitis and cholera.

In the last decade, an even more menacing and lethal virus, the Acquired Immune Deficiency Syndrome, or AIDS virus, could be communicated by such accidental and catastrophic event. Since there is no known cure for AIDS at this time, a great deal of precaution is required to prevent the accidental prick of the health care provider by an insertion needle which has previously been used on a patient.

Many types of syringes of one type or another have been developed in an effort to address this problem yet allow the ease of use of more conventional hypodermic needles.

A search of the prior art did not disclose any patents that read directly on the claims of the instant invention. However, the following U.S. Patents were considered related:

| U.S. Pat. No. | Inventor | Date Issued |
| --- | --- | --- |
| 3,046,985 | Saenz, O | July 31, 1962 |
| 3,134,380 | Armao, T. | May 26, 1964 |
| 3,306,290 | Weltman, H. S. | Feb. 28, 1967 |
| 3,890,971 | Leeson, T. A. | June 24, 1975 |
| 4,367,738 | Legendre, R. | Jan. 11, 1983 |
| 4,416,663 | Hall, R. N. | Nov. 22, 1982 |
| 4,631,057 | Mitchell, C. B. | Dec. 23, 1986 |
| 4,695,274 | Fox, R. L. | Sep. 22, 1987 |
| 4,702,739 | Milorad, N. M. | Oct. 27, 1987 |
| 4,731,068 | Hesse, J. E. | Mar. 15, 1988 |
| 4,735,618 | Hagen, J. | Apr. 05, 1988 |
| 4,737,144 | Choksi, P. V. | Apr. 12, 1988 |
| 4,737,150 | Baeumle, H. | Apr. 12, 1988 |
| 4,738,663 | Bogan, D. E. | Apr. 19, 1988 |
| 4,743,233 | Schneider, M. | May 10, 1988 |
| 4,747,829 | Jacob, et al | May 31, 1988 |
| 4,747,830 | Gloyer, et al | May 31, 1988 |
| 4,747,831 | Kulli, J. C. | May 31, 1988 |
| 4,752,290 | Schramm, J. J. | June 21, 1988 |
| 4,755,170 | Golden, T. A. | July 05, 1988 |
| 4,772,272 | McFarland, B. C. | Sep. 20, 1988 |
| WO 89/00435 (PCT) | Gaarde, K. W. | Jan. 26, 1989 |

U.S. Pat. No. 3,046,985, issued to C. Saenz on Jul. 31, 1962, discloses a dental syringe adapter for concealing a needle of the hypodermic syringe prior to use by a dentist. The needle is retained in a housing until a syringe plunger is depressed and the needle is pushed out of the protective housing instead of being captively retained within a syringe body.

U.S. Pat. No. 3,134,380, issued to T. Armao on May 26, 1964, discloses a hypodermic syringe needle having a shield which need not be removed prior to the use of the needle and which can be disposed of along with the needle itself. Holes are provided near the end of the shield to permit the escape of air as the shield is collapsed, allowing the needle to protrude through the protective caps. The cap is held in an extended position by a spring which yields upon injection.

U.S. Pat. No. 3,306,290, issued to H. S. Weltman on Feb. 28, 1967, discloses a retractable needle syringe which retracts the needle into a fluid-containing body and not into the syringe plunger.

U.S. Pat. No. 3,890,971, issued to T. A. Leeson on Jun. 24, 1975, discloses a safety syringe for one-time use, including a plunger which is lockable by detent members and a slidable needle cap which is also permanently lockable to prevent reuse. The needle cap slides over the exterior of the syringe barrel and over the fixed needle.

U.S. Pat. No. 4,367,738, issued to R. Legendre on Jan. 11, 1983, discloses a pre-filled syringe having spikes upon the plunger rods to prevent the withdrawal of the plunger from the syringe barrel. No means is disclosed for protecting the user from accidental pricking with the tip of the needle.

U.S. Pat. No. 4,416,663, issued to R. N. Hall on Nov. 22, 1983, discloses a self-sterilizing needle, wherein a capsule containing sterilizing fluid and having perforated ends of flexible material with elastic memory tendencies for self sealing after actual penetration by the forward end of the needle. The capsule is coaxially and slidably received over the forward end of the needle, with the forward exposed end of the needle slidably penetrating one end of the capsule and perforation for sterilizing of the needle. A syringe is provided for axially urging and positioning the capsule outward to its original position of rest. Then, the exposed end of the needle is again enclosed in the capsule for sterilization when the hypodermic penetration force is removed.

U.S. Pat. No. 4,631,057, issued to C. B. Mitchell on Dec. 23, 1986, discloses a needle coupled to a syringe barrel, wherein a needle guard is mounted on the barrel for movement from a retracted position in which the guard does not shield the needle, to an extended position in which the guard shields the needle.

U.S. Pat. No. 4,695,274, issued to R. L. Fox on Sep. 22, 1987, discloses a safety needle attachment wherein the needle is initially and entirely surrounded by a protecting jacket which is releasably interlocked with a holder. When the needle is to be used, an interlocker is released and the Jacket is effectively telescoped over the holder to project the needle through a membrane over the end of the jacket to a working position.

U.S. Pat. No. 4,702,739, issued to N. M. Milorad on Oct. 27, 1987, discloses a hypodermic needle having a sleeve extending from a holder protectively covering the needle so that the sleeve can be placed against the body part where injection is to occur and with the needle tip proximate to the body part. By sliding the holder toward the body part, a detent restraint holding the sleeve in an extended position is overcome and relative retraction movement effected therewith.

U.S. Pat. No. 4,731,068, issued to J. E. Hesse on Mar. 15, 1988, discloses a non-reloadable syringe wherein the plunger is permitted to be withdrawn for purposes of loading the syringe and permitted to be urged forward to discharge the contents of the syringe. However, means is provided wherein subsequent retraction of the plunger assembly is inhibited to prevent further loading and use of the syringe.

U.S. Pat. No. 4,735,618, issued to J. Hagen on Apr. 5, 1988, discloses a protective enclosure for a hypodermic syringe needle formed by a tubular sleeve sized for friction fitting engagement over the barrel portion of the syringe. A needle guard portion is located at an opposed end, and pivotally removable arms operate to permit the needle to pass through a central channel of the needle guard.

U.S. Pat. No. 4,737,144, issued to P. V. Choksi on Apr. 12, 1988, discloses a syringe system comprising a tubular barrel and a sleeve mounted on the barrel to slide lengthwise from a retracted position in which the needle is exposed, to an extended position in which the sleeve extends protectively about the needle.

U.S. Pat. No. 4,737,150, issued to H. Baeumle on Apr. 12, 1988, discloses a tube-cannula syringe, the first cannula being disposed so as to be displaced relative to the second cannula, to be removable or displaceable in the longitudinal direction of the syringe.

U.S. Pat. No. 4,738,663, issued to David E. Bogan on Apr. 19, 1988, discloses a sleeve guide having a pair of fasteners with cavities formed in them that fit over the flange and which are located in hypodermic syringes for grasping in the user's fingers. The guide in the retracted position prevents the accidental pricking by the needle.

U.S. Pat. No. 4,743,233, issued to Michael B. Schneider on May 10, 1988, discloses a slidable sleeve over a syringe barrel that is connectable in a first position extending over a hypodermic needle and that is reconnectable in a second position along the syringe barrel to expose the needle for use.

U.S. Pat. No. 4,747,829, issued to J. Jacob et al., on May 31, 1988, discloses a pre-filled syringe with a retractable needle. A barrel of the syringe is removable within a casing from a remote pre-injection position to a forward injection position and back again. The barrel is moved forward allowing the needle to pass through an opening in a cap prior to injection.

U.S. Pat. No. 4,747,380, issued to W. W. Gloyer et al., on May 31, 1988, discloses a syringe having a hollow barrel formed at the distal end to receive an injection piston carried by the plunger member which allows the needle to also retract within the barrel by extracting the piston.

U.S. Pat. No. 4,747,831, issued to John C. Kulli on May 31, 1988, discloses a cannula insertion needle housing. The housing includes a latch mechanism for extending and retracting the needle.

U.S. Pat. No. 4,752,290, issued to J. J. Schramm on Jun. 21, 1988, discloses a tubular shield which is adapted to protect users from injury. The tubular shield cooperates with the raised surfaces on the body of the medical appliance to be protected.

U.S. Pat. No. 4,755,170, issued to T. A. Golden on Jul. 5, 1988, discloses a protective sealing device comprising a block with which a sharp end of the needle can be held within to prevent accidental puncture. Also disclosed is a retaining shield which can be retracted over the needle to prevent accidental puncture.

U.S. Pat. No. 4,772,272, issued to B. C. McFarland on Sep. 20, 1988, discloses a protective sleeve for a hypodermic needle which sleeve is completely dissociable from the hypodermic syringe. The protective sleeve is moved over the needle protecting position to the needle injection position solely by axial movement of the protective sleeve.

An International Patent Application filed by K. W. Gaarde and having a published number WO 89/00435, and a publication date of Jan. 26, 1989, shows a hypodermic syringe with a retractable needle in a needle holding mechanism which is integrally attached to a syringe body.

It is desirable that the insertion needle of the hypodermic needle or intravenous catheter device can be made available in a safe condition prior to insertion so that the health care provider will not accidentally prick his/her finger and require a new sterilized needle prior to the insertion into the patient. It is also a requirement that after insertion or sampling using the insertion needle, that the needle be safely and easily discarded without representing a continued health risk to anyone who may encounter the insertion needle, either on the premises of the health care facility, or in transit or arrival at the refuse collection area or disposal facility.

There is potentially a great interest in the health care industry to manufacture, sell, distribute, and use a hypodermic needle, an intravenous catheter insertion needle and a vacuum tube syringe that provides the type of safety as described above. It can be easily operated, proves to be completely reliable, and is easily and cheaply manufactured, yet still has a great deal of versatility for various applications using various needles in diameter and length and different sized vacuum tubes.

The features described above as being desirable for hypodermic syringes, intravenous catheter insertion devices and vacuum tube syringes are all provided for by the present invention.

DISCLOSURE OF THE INVENTION

The present invention is embodied in an approved hypodermic syringe system and intravenous catheter insertion device which is entirely safe prior to insertion or sampling due to a protective cover tip. Furthermore, after insertion or sampling, the hypodermic syringe system and intravenous catheter insertion device is entirely safe, since the health care provider, using one hand, can retract the insertion needle into a tamperproof isolation container which may then be easily and safely discarded, preventing the injury or transmission of any dangerous viruses or bacteria. In addition, both the hypodermic syringe system and intravenous catheter insertion device are easily manufactured, easy to use and provides visual and audible confirmation that the insertion needle has been safely retracted after use.

More particularly, the hypodermic injection system comprises a cylindrical syringe housing assembly, holding a retractable injection needle which can be safely, quickly and easily retracted within a specially designed syringe plunger. Furthermore, the plunger is fixedly held after use within a specifically designed syringe barrel. The syringe barrel, plunger and needle assembly can be easily discarded without the dangers associated with an exposed needle or needle that can be easily uncapped. The needle is held locked inside the barrel which is tamperproof.

In a more specific description of the invention, the injection needle has a sharp end, a shaft with an axial passageway therethrough, and a holder defining a raised plastic lip seal. The injection needle is mounted within a cylindrical spring housing assembly having frangible and resilient fingers which are spreadable radially outward on a first end and extending tabs that extend radially outward on an external surface of the cylindrical needle housing.

Thus, a mechanism is provided for associating the cylindrical spring housing with the syringe barrel in a locking manner. Once the needle assembly is fully threaded, any attempt to unscrew the needle assembly is impeded by a one way locking finger on the needle housing. The cylindrical spring housing includes a first sealing means for providing a seal between the cylindrical spring housing and the holder of the hypodermic injection needle. Also, a second sealing means for providing a seal between the cylindrical spring housing and the syringe barrel is used.

An opening in a second end of the cylindrical spring housing is sized to receive the shaft of the injection needle while retaining the holder when both are forwardly positioned within the cylindrical spring housing assembly. The frangible and resilient fingers of the spring housing have radially inwardly positioned hooks sized to engage and hold the raised sealing lip of the holder of the injection needle when the shaft of the injection needle is forwardly located within the cylindrical spring housing. The hooks have inwardly tapered shoulders so as to be easily spread by complementing and an outwardly positioned conical shoulder of the syringe plunger.

A coiled spring is positioned axially within the cylindrical spring housing assembly between the holder and the second end of the cylindrical spring housing. The spring exerts an expansive force between the holder of the insertion needle and the second end of the cylindrical spring housing, a force which is less than the retaining force exerted by the hooks of the frangible and resilient or frangible fingers, thereby retaining the insertion needle within the cylindrical spring housing against the expansive force of the spring.

The syringe barrel includes helical threads sized and positioned to receive the extending locking tabs of the cylindrical spring housing and the second sealing means to provide a pressure tight seal between an interior tapered surface of the cylindrical spring housing and an exterior tapered wall of the barrel. The interior of the barrel is shaped sufficient to engage the cylindrical spring retainer and allow the resilient legs to flex radially outward or the frangible fingers to fracture and then resiliency flex outwardly.

The syringe plunger is sized to be received concentrically within the syringe barrel and has a hollow, axially located chamber therein. The syringe plunger has a frangible end plug located within outwardly tapered conical shoulders adjacent to the chamber. The frangible end plug disassociates from the syringe plunger upon contact with the needle holder and is injected into the hollow chamber when the outward tapered conical shoulders forcibly engage the inwardly tapered shoulders of the hooks of the frangible and resilient fingers, thereby spreading the fingers outwardly and disengaging the hooks from the raised lip of the holder of insertion needle. The frangible end dissociates under a predetermined normal force between the holder of the isertion needle and the frangible end. This allows the coiled spring to eject the syringe needle from the cylindrical spring housing into the chamber within the plunger.

Optionally, the chamber located within the syringe plunger may be evacuated so that when the frangible end breaks and ejects with the needle into the chamber, any peripheral fluid is also drawn into the chamber and away from the cylindrical spring housing.

Furthermore, an outwardly-oriented ring or lip on the exterior of the plunger is positioned so as to engage a complementing recess or radial groove within the interior of the syringe barrel when the plunger is in a fully-depressed position to lock the plunger within the syringe barrel, preventing its removal and access to the retained needle therein.

The holder of the needle can have a bright color (such as red) so as to be visually distinctive within the transparent syringe barrel and syringe plunger, so that the health care provider can readily determine that the syringe is in a safe condition for transport or discard. The exterior of the syringe barrel can also be fitted with a color-coded sizing ring, which quickly and clearly identified the size or capacity of the syringe system.

In a second embodiment, the needle ejecting mechanism can be held on the end of the syringe plunger. In that configuration, the needle is retained by a frangible needle holder associated with the ejection end of the syringe barrel. The hypodermic needle has a head which can be readily grabbed by a modified end of the syringe plunger. Depression on the syringe plunger dissociates the needle from the frangible needle holder. Further depression on the syringe plunger allows a needle retractor to pass by engaging detents, while a similar coiled spring ejects the needle retractor which is now engaging the needle, ejecting the needle into the interior chamber of the syringe plunger.

A third embodiment of the invention uses the same principles as the preferred embodiment except the attachment of the spring housing is slightly different and the hollow end in the plunger is larger. Other minor differences simplify the structure somewhat.

In a fourth embodiment for taking blood samples, the barrel is basically the same along with the hypodermic needle with the holder and the coiled spring. The plunger however, is much shorter and contains a hollow linking needle on the inside end. A standard sampling fluid vacuum container is inserted into the barrel and impinges on the linking needle through a resilient cap like seal creating a flowpath for the blood sample through the hypodermic injection needle. When the sample has filled the container, the extending end is forced into the barrel with the user's thumb. The tapered end of the plunger forcibly spreads the resilient fingers holding the injection needle outward releasing the needle against the expansive force of the coiled spring. This action permits the spring to extend into the hollow syringe plunger retracting the needle inside as in the preferred embodiment.

In a fifth embodiment of the invention, an intravenous catheter insertion device uses the same principles as the preferred embodiment except the spring housing assembly is modified and the plunger and barrel have been simplified.

The intravenous catheter insertion device comprises a spring housing assembly without the sealing means of the preferred embodiment, holding a retractable insertion needle which also is safely, quickly, and easily retracted within a similarly designed plunger which is fixedly held after use within a modified barrel as previously described.

In a more specific description of this embodiment, the intravenous catheter insertion device has a catheter hub comprising a flexible catheter sleeve having a shaft with an axial passageway therethrough wherein an insertion needle is concentrically located having a needle holder affixed at a distal end and a sharp end at the tip. The insertion needle is mounted within a spring housing assembly having resilient or frangible fingers which are spreadable radially outward on a first end and includes external guiding tabs for insertion needle orientation, and a circumferential locking groove on an external surface and one way locking ratchet teeth in the barrel. Thus, a similar mechanism is provided for associating the spring housing assembly with a barrel in a locking manner.

An opening in a second end of the spring housing assembly is sized to receive a housing plug having a front end aperture to allow passage of the shaft of the insertion needle, while retaining the needle holder and spring in the first end when both are forwardly positioned within the spring housing assembly. The resilient or frangible fingers of the spring housing assembly have similar radially inwardly positioned hooks, as used in the preferred embodiment, sized to engage and hold the end of the needle holder of the insertion needle when the shaft of the insertion needle is forwardly located within the first end of the spring housing assembly. The coiled spring is positioned axially within the spring housing assembly between the needle holder held by the hooks, and by affixing the housing plug to the second end of the spring housing assembly. The spring exerts the same expansive force between the needle holder of the insertion needle and the front end of the housing plug as in the preferred embodiment, thereby retaining the insertion needle within the spring housing assembly against the expansive force of the spring.

The barrel is modified to have ratchet teeth sized and positioned to receive the external locking groove of the spring housing assembly and a transparent viewing lens for the doctor or nurse to view blood, indicating that the insertion needle and catheter sleeve are located properly into the vein. The interior of the barrel is shaped sufficiently to engage the spring housing assembly and allow the resilient fingers to flex radially outward.

The plunger is sized to be received concentrically within the barrel having an external ring portion for providing a semi-sealing means for venting air between the exterior surface of the plunger and the interior surface of the barrel, and the plunger has a hollow, axially located chamber therein. The plunger has a frangible end plug at a forward end, located within outwardly tapered conical shoulders adjacent to the chamber, wherein the outwardly tapered conical shoulders are shaped to engage and spread complementary inwardly tapered shoulders of the hooks as described in the preferred embodiment.

Once again, in operation the frangible end plug disassociates from the plunger upon contact with the needle holder and is injected into the hollow chamber when the outwardly tapered conical shoulders forcibly engage the inwardly tapered shoulders of the hooks of the resilient or frangible fingers, thereby spreading the fingers outwardly and disengaging the hooks from the end of the needle holder of the insertion needle. The frangible end dissociates under a pre-determined normal force between the needle holder of the insertion needle and the frangible end. As described before, this allows the coiled spring to eject the insertion needle from the spring housing assembly into the chamber within the plunger.

Furthermore, a rachet on the exterior of the plunger is positioned so as to engage a complementing recess or radial groove within the interior of the barrel when the plunger is in a fully-depressed position to lock the plunger within the barrel, preventing its removal and access to the retained incisional needle therein.

The hypodermic syringe system and intravenous catheter insertion device of the present invention provides for a retractable needle which is durable, disposable, easy to manufacture, prevents the accidental pricking after use, and provides for greater ease of handling the hypodermic or insertion needle after use, including the subsequent discarding of the device. The intravenous catheter insertion needle is extremely simple in construction, yet completely effective in placing a catheter sleeve for injecting fluid into a vien subsequently becoming completely safe after use while the health care provider need only use one hand to retract the insertion needle, leaving his other hand free. Furthermore, his or her fingers may remain in their relative positions to retract the needle.

Other aspects and advantages of the present invention will be apparent from the following description of the preferred embodiments, taken in conjunction with the accompanying drawings, which illustrate, by way of example, the principals of the invention.

BRIEF DESCRIPTION OF THE DRAWINGS

FIG. 7 is an exploded view of the hypodermic syringe in the third embodiment.

FIG. 8 is a cross-sectional view of the hypodermic syringe of the third embodiment of the present invention shown with the plunger open ready for use.

FIG. 9 is a cross-sectional view of the hypodermic syringe of the third embodiment of the present invention with the plunger in the fully depressed position and the needle fully retracted.

FIG. 10 is an exploded view of the hypodermic syringe in the vacuum tube blood sampling embodiment.

FIG. 11 is a full cross-sectional view of the hypodermic syringe in the vacuum tube blood sampling embodiment shown with the vacuum tube installed in the device and the hypodermic needle extended ready for use and the cap removed.

FIG. 12 is a full cross-sectional view of the hypodermic syringe in the vacuum tube blood sampling embodiment with the tube removed and the needle retracted ready for disposal.

BEST MODE FOR CARRYING OUT THE INVENTION

Figure 1:
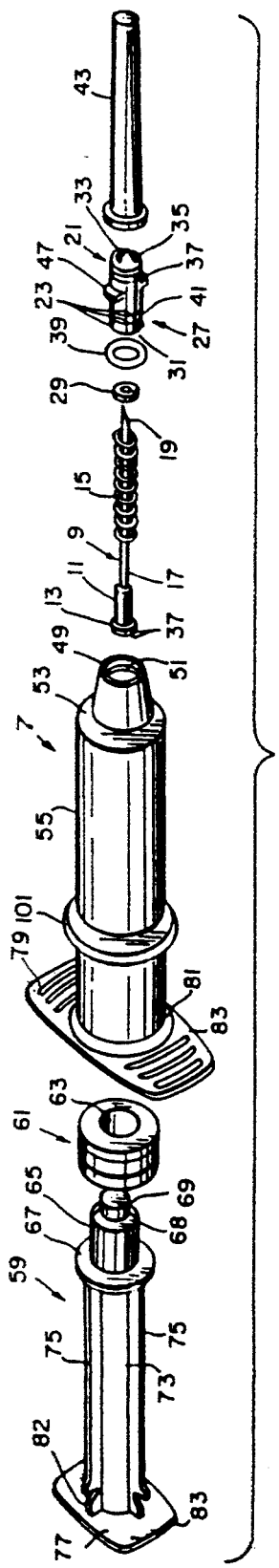
FIG. 1 is an exploded view of the hypodermic syringe of the present invention.
Figure 2:
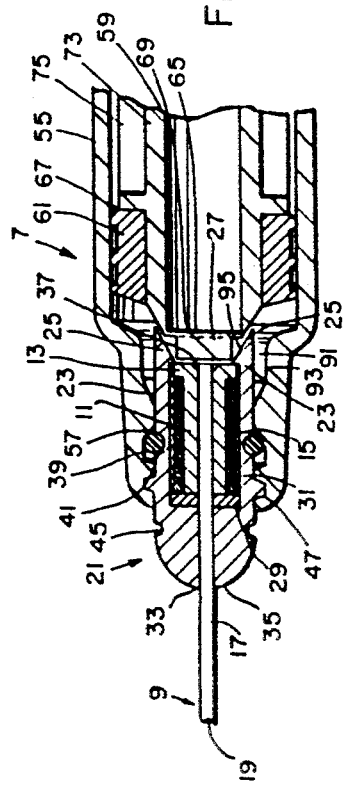
FIG. 2 is a partial cross-sectional view of the hypodermic syringe of the present invention shown with its plunger proximate to the needle housing.

The best mode for carrying out the invention is presented in the terms of a preferred, second, third, fourth and fifth embodiment. All five embodiments are basically identical in principle and function, however, slight variations in structure segregate the five. The preferred embodiment is shown in FIGS. 1-6, wherein like numerals represent like elements throughout, the complete hypodermic syringe 7 of this embodiment is best shown in exploded view as FIG. 1. The main components of syringe 7 are a standard injection needle 9 having a specifically mounted holder 11 including an enlarged lip 13, located posteriorly thereto. A coiled spring 15 rides a shaft 17 of the injection needle 9 with an axially located passageway 19 therethrough. A cylindrical spring housing 21 includes a plurality of radial spaced resilient fingers 23 which include inwardly engaging an inferiorally positioned hooks 25 on the posterior end 27 of the spring housing 21. A sealing means or washer 29 is sized to be received within an inner cavity 31 of the spring housing 21.

The injection needle 9, including the enlarged lip 13 of the holder 11 can be forwardly positioned within the inner cavity 31 of the cylindrical spring housing 21. A cross-shaped opening 33 in a forward end 35 of the spring housing 21 allows the shaft 17 of the injection needle 9 to extend through the cross-shaped opening 33. The enlarged lip 13 is engaged by the hooks 25 when forwardly positioned within the spring housing 21, causing the resilient fingers 23 and hooks 25 to flex around the enlarged lip 13 and engage a top surface 37 of the enlarged lip 13.

The washer 29 provides a secure seal between the shaft 17 of the injection needle 9 and the inner cavity 31 of the spring housing 21. Finally, a gasket or O-ring engages a circumferential groove 41, located midway between the posterior end 27 of the spring housing 21. This configuration can be more clearly shown in FIG. 2, and also in FIG. 3, partially exploded from the other components of the hypodermic syringe 7 of the present invention.

Figure 3:
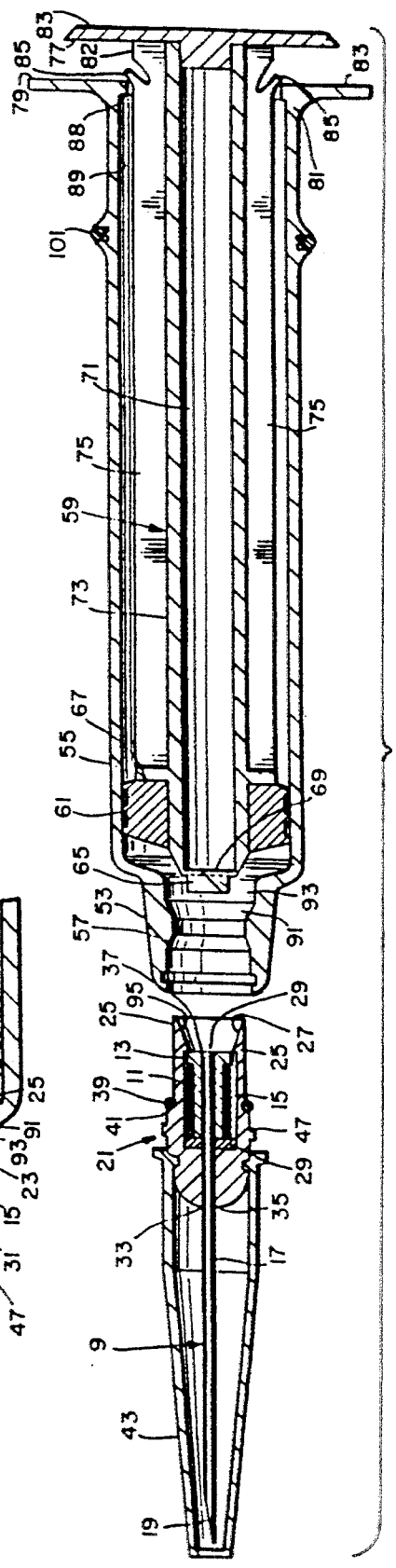
FIG. 3 is a cross-sectional view of the hypodermic syringe of the present invention with the needle housing, needle, and needle cap shown exploded from the syringe barrel.
Figure 4:
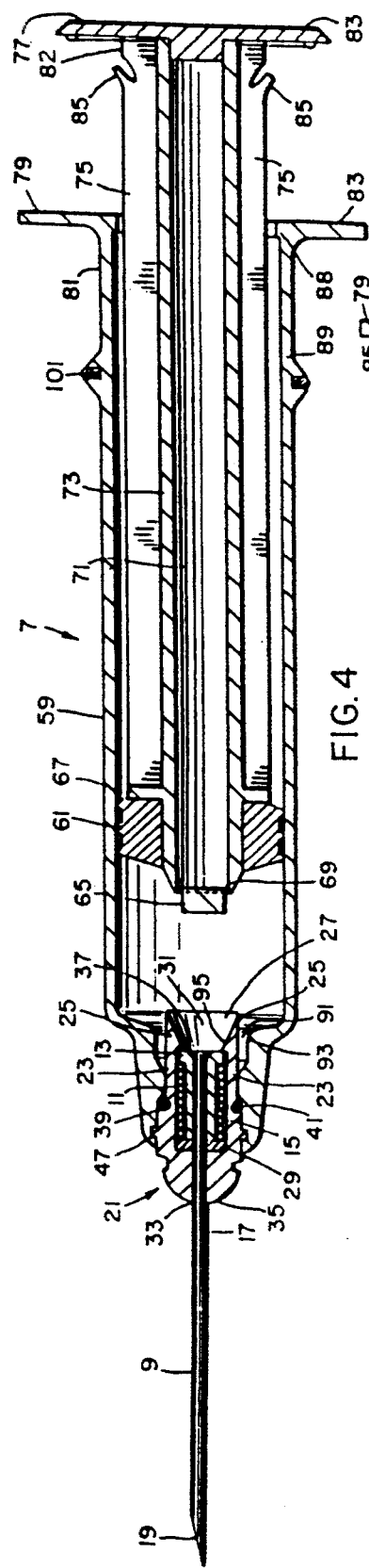
FIG. 4 is a cross-sectional view of the hypodermic syringe in the present invention shown with the syringe plunger in a partially depressed position within the syringe barrel.
Figure 5:
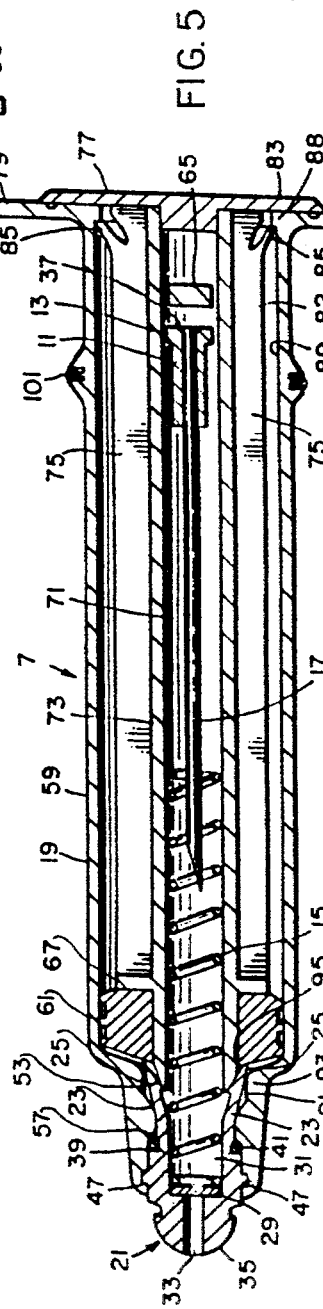
FIG. 5 is a cross-sectional view of the hypodermic syringe of the present invention shown with the syringe plunger in a fully depressed position and the needle fully retracted.

Also, shown in FIG. 3 is a needle cap 43, which engages a forwardly-positioned second circumferential groove 45 of the spring housing 21. The spring housing 21 has radially-extending bayonet slots 47, which provide locking engagement within bayonet slots 49 and a bayonet groove 51, located within a tapered nose 53 of a syringe barrel 55. Engagement between the spring housing 21 and the tapered nose 53 of the syringe barrel 55 is easily accomplished by aligning the bayonet tabs 47 with the bayonet slots 49 and pushing the spring housing 21 through the bayonet slots 49 and then rotating the bayonet tabs 47 within the bayonet groove 51 to provide locking engagement therebetween. The bayonet tabs 47 may have slanted edges (not shown) on opposing sides and the bayonet groove may have raised surfaces (not shown) to allow the slanted edges to pass by the raised surface in one direction of rotation. This effectively locks the spring housing 21 to the tapered nose 53 of the syringe barrel 55 in a racket-like manner.

The first tapered inner wall 57 within the tapered nose 53 of the syringe barrel 55 provides sealing engagement between the spring housing 21 and the syringe barrel 55, due to the tight fit of the O-ring 39 between the spring housing 21 and the first tapered inner wall 57.

A plunger 59 is sized to be received within the syringe barrel 55 and engages a plunger piston 61 of a conventional type commonly used with syringe systems known in the art, except that a cylindrical cavity 71 extends therethrough, allowing a frangible end 65 to enter the cylindrical cavity 71 of the plunger piston 61. The plunger piston 61 is positioned over the associated frangible end 65 and is supported by a rim 67. The length of the plunger piston 61 is such that outwardly tapered shoulders 68 extend through and above the passageway 63 of the plunger piston 61, joining the frangible end 65. Between the outwardly tapered shoulders 68 and the frangible end 65 is a circumferential groove 69 of a defined thickness of approximately 0.031 inches (0.080 cm) which allows the frangible end 65 to dissociate from the outwardly tapered shoulders 68 upon a normal force on the frangible end 65 of approximately two pounds or less in the preferred embodiment. The circumferential groove 69 can, of course, simply be a thinner construction of material allowing frangibility.

The plunger 59 includes the cylindrical central cavity 71 running axially through the plunger 59 and adjacent to the frangible end 65. The cylindrical cavity 71 has a diameter sufficient to allow the enlarged lip 13 and the holder 11 and the associated shaft 17 of the injection needle 9 to be injected into the cylindrical cavity 71 and need not be circular. Furthermore, the cylindrical cavity 71 can be evacuated so as to allow the vacuuming effect upon the dissociation of the frangible end 65 from the outwardly tapered shoulder 68.

A plunger sleeve 73 defines the cylindrical cavity 71 while reinforcement ribs 75 provide support to the plunger sleeve 73 and are associated with the rim 67 to provide additional support when the plunger 59 is being depressed. A pushing plate 77 is located on a posterior end 82 of the plunger 59. The pushing plate 77 is sized sufficient to allow the thumb of a normal person to properly depress the plunger 59 when associated with the syringe barrel 55.

Also, finger retaining lips 79 are associated with the posterior end 81 of the syringe barrel 55 so as to allow the index finger and middle finger to grasp the finger-retaining lips 79 of the syringe barrel 55 while the thumb presses upon the pushing plate 77. Grooves 83 or knurling may be etched within the finger-retaining lips 79 or upon the pushing plate 77 to provide a greater coefficient of friction between the fingers and thumb and the finger retaining lip 79 and pushing plate 77, respectively.

Radially extending ratchet teeth 85 interrupt the reinforcing ribs 75 and are posteriorly located while being posteriorly flared to allow the ratchet teeth 85 to pass by an extending ratchet lip 88 defined by an interior wall 89 of the syringe barrel 55. Upon full depression of the syringe plunger 59 within the syringe barrel 55, the ratchet teeth 85 pass by the ratchet lip 88. The ratchet teeth 85 flexibly pass by the ratchet lip 88 and prevent the extraction of the plunger 59 from the syringe barrel 55.

In operation, the syringe 7 of the instant invention, functions very much like a conventional hypodermic syringe as found in the prior art. However, after injection, of the substance to be injected the hypodermic syringe 7 of the instant invention allows the dissociation of the frangible end 65 from the outwardly tapered shoulders 68 of the plunger 59 and the radial flexing of the resilient fingers 23 so that the hooks 25 release the enlarged lip 13 of the holder 11 of the injection needle 9.

Since a circumferential space 91 exists between the resilient fingers 23, and the inner wall 93 of the syringe barrel 55, the resilient fingers 23 can flex, releasing the holder 11. The resilient fingers will only flex when inwardly tapered surfaces 95 of the hooks 25 are engaged by the outwardly tapered shoulders 68 of the plunger 59. Such engagement takes place when the plunger 59 is pushed through the syringe barrel 55 and the frangible end 65 abuts against the top surface 37 of the holder 11. A normal force of less than 2 pounds exerted between the top surface 37 of the holder 11 and the frangible end 65 causes the frangible end 65 to dissociate from the outwardly tapered shoulders 68 of the plunger 59.

With the resilient fingers 23 flexed radially outward, causing the hooks 25 to release the holder 11, the compressed spring 15 exerts an ejecting force against the enlarged lip 13 of the holder 11, propelling the injection needle 9 along with the holder 11, as well as the dissociated frangible end 65 into the cylindrical cavity 71 of the plunger 59.

The above operation makes a very distinctive click sound alerting the health care provider that the device is now safe.

Also, if the cylindrical cavity 71 is evacuated, a suction pulls the residual fluids into the cylindrical cavity 71. Upon further depressions of the syringe plunger 59 into the syringe barrel 55, the ratchet teeth 85 engage the ratchet lip 88, preventing the plunger 59 from being extracted from the syringe barrel 55.

The holder 11 can be a bright red or fluorescent color, while the plunger 59 and syringe barrel 55 can be manufactured from a transparent or translucent material so that the retracted position is readily identified in low light conditions and the needle is visibly safe for further handling, transport of discard.

Also, an interchangeable identification ring 101 can be positioned around the syringe barrel 55 so as to identify the hypodermic syringe for whatever purpose.

The plunger 59, syringe barrel 55, holder 11, spring housing 21 and needle cap 43 can be made from a transparent or translucent plastic material. However, the spring housing 21 does not necessarily have to be transparent nor does the holder 11. Such materials and their manufacturer are well known in the art and will not be further herein described. The plunger piston 61 can be formed of a neoprene material sufficient to provide a seal between the plunger piston 61 and the syringe barrel 55 and is also commonly known in the art and will not be hereinafter described in more detail. The shaft 17 of the injection needle 9 is of material known in the art as well.

The O-ring 39 can be of a elastomeric material, just as the washer 29 may also be of a resilient material, so as to provide a proper sealing effect well known in the art. It should be noted that the spring housing 21 must be formed of a durable plastic material which is resilient, so that the resilient fingers 23 properly and radially outwardly extend in association with the syringe plunger 59. The syringe plunger must be of a more resilient or brittle material or have a proper thickness so as not to flex inwardly when the frangible end 65 dissociates from the plunger 59. It is important that the plunger 59 remains sufficiently durable to cause the resilient fingers 23 to move radially outward when the inwardly tapered surfaces 95 of the hooks 25 engage the outwardly tapered shoulders 68 of the syringe plunger 59. Specific examples of types of plastics and thicknesses are not required, as these can be readily determined by those ordinarily skilled in the art of plastics manufacture.

Figure 6:
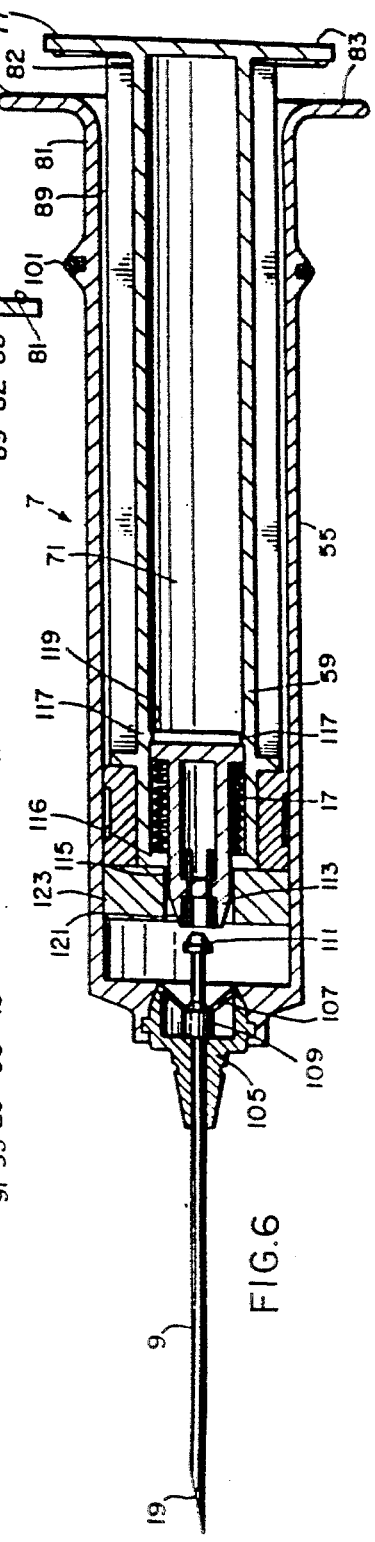
FIG. 6 is a cross-sectional view of the second embodiment of the hypodermic syringe of the present invention.

In the second embodiment, the mechanism responsible for ejecting the injection needle 9 can be fully positioned within the syringe plunger 59. As shown in FIG. 6, some slight variations in structure are necessary to achieve similar if not identical results as described in the first embodiment of the invention.

The injection needle 9 is held within a frangible needle holder 105, which includes a frangible cone 107, which engages an enlarged section 109 of the injection needle 9. The injection needle 9 has a length sufficient to extend well within the syringe barrel 59 and has an extraction end 111, which can be engaged by extraction hooks 113 of similar design as shown in FIGS. 1–5.

A needle retractor housing 115 is located and held on an inward end of the syringe plunger 59, specifically held in place by detentes 117, defined within the interior wall 119 of the cylindrical cavity 71 of the plunger 59. The compressed spring 17 exerts force between the needle retracting housing 115 and the inner end 116 of the plunger 59. The force exerted by the spring is not sufficient to force the needle retractor housing 115 past the detents 117.

In operation the plunger 59 is pushed into the barrel 55 having outwardly tapered shoulders 121, which break the frangible cone 107, thereby releasing the enlarged section 109 of the injection needle 9. Further downward pressure on the plunger 59 forces the needle retractor housing 115 past detentes 117, allowing the spring 15 to expand, pushing the needle retractor housing 115 deep within the cylindrical cavity 71 and taking with it the injection needle 9, because the hooks 113 grab the extraction end 111 as the needle retractor housing 115 is moved deeper into the cylindrical cavity 71 of the plunger 59. It should be noted that an extra piston spacer 123 is required for proper operation, due to the injection needle 9 extending within the syringe barrel 55.

Besides the above-identified differences, the second embodiment of the invention functions substantially as the first and the materials necessary for each of the components are similar to those materials as described in the first embodiment of the invention.

The third embodiment of the invention is illustrated in FIGS. 7-9 and consists of a syringe barrel 55' having a partially open end 125 and a fully opened end 127. The barrel 55' has finger retaining lips 79' on the partially opened end 125 providing a gripping surface for the user's fingers. Optionally, near the lips 79', a color coded ring 101 of sufficient resilient and diameter is slid over the exterior surface of the barrel 55' and retained by friction to identify and particular syringe system. The open end 125 of the barrel contains bayonet slots 49' and grooves 51' or threads for connecting other elements to the open end. The barrel 55' is transparent thus, permitting the user to see the fluid inside allowing expulsion of bubbles of air that may be within the liquid dispensed by the syringe.

A hollow syringe plunger 59' is slidably received within the barrel 55' and is sized to move linearly back and forth without restriction. The plunger 59' has converging taper 135 on one end and an axial flange 136 on the other. The flange 136 has a radially thinned slender section 138 at the interface with the barrel 55' which actually breaks away if forced outwardly when the plunger 59' is in its fully closed position contiguous with the barrel 55'.

A resilient barbed stopper 140 is tightly pressed into the flange end of the plunger 59' completely closing the end thereof allowing a hermetic seal inside the plunger. A frangible end 65' is located on the tapered end 135' of the plunger 59' completing the hermetic seal inside. The plunger 59' further contains an outwardly extending raised circumferential band 142 around the flange end and the barrel 55' has an internal recessed girdle 144 in a similar location near the lips 79'. When the plunger 59' is fully depressed and is recessed flush with the end of the barrel 55', the band 142 snaps into the recessed girdle 144 locking the plunger 59' into place. This prevents the plunger from being withdrawn and as the flange 136 is frangible, the closure becomes tamperproof even if an attempt is made to pry the flange 136 from the barrel 55'.

On the converging tapered end 135 of the plunger, a piston 61' is positioned over a raised radial project 146. This piston is resilient in nature and seals the internal portion of the barrel 55' allowing liquids to be drawn inside and forced out by the movement of the plunger 59'. Initially, the piston 61' is located such that it is forward of the tapered end 135, however, when the plunger 59' is fully inserted into the barrel 55', the piston 61' is forced over the radial projection 146 into a secondary position sealing tightly against the inside of the hollow of the barrel 55' and exposing the tapered end 135 of the plunger 59'.

An injection needle 9' is positioned into the partially opened end 127 of the barrel 59'. This needle 9' has an axial passageway inside and is sharp on the exposed end and flat on the other, or holder end. Spring holding means in the form of a holder 11', coiled spring 15' and spring housing 21' retain the needle 9' and attach combined elements to the barrel 55'. The holder 11' has a raised lip 13' on the end and the spring housing 21 is divided into two pieces 21a and 21b that are pressed together. The front portion 21a attaches to the barrel with bayonet tabs 47' into the threads consisting of slots 49' and grooves 51' and partially retains the spring 15'. The rear portion 21b retains the balance of the spring 15' and fingers 23' and hooks 25' are integrally formed therein in a frangible manner. The needle holder 11' is held in place as the lip 13' interfaces with the hooks 15' on the fingers 23' maintaining compressive tension on the spring 15'.

In operation, the fluid medication or pharmaceutical is drawn into the syringe 7' in a normal manner by the vacuum created when the plunger 59' is withdrawn. After injecting the liquid and the needle is withdrawn, the plunger 59' is forced completely into the barrel 55'. As the tapered end 135 of the plunger approaches the end of the hollow barrel 55', the piston 61' is forced back over the raised projection 146 and simultaneously, the plunger converging taper end 135 forcibly breaks the frangible section between the resilient fingers 23' of the rear portion 23b of housing 21'. This forcible bending outward of the resilient fingers 23' releases the holders raised lip 13' held by the hooks 25 at the end of the fingers 23'. This releasing movement permits the expansive force of the coiled spring 15' to break the frangible end 65' of the plunger 59' and drive the needle 9' frangible end 65' and spring 15' into the hollow of the syringe plunger 59' fully retracting the needle 9' and retaining it safely inside the syringe 7'. An audible clicking sound is heard when this action takes place. As previously described, the plunger 59' is fully inserted into the barrel 55' with the flange 136 flush with the open end 125 of the barrel 55' and is unremovable due to the locking into place of the band 142 into the girdle 144. As it is seen, the elements and function of this embodiment are basically the same with only slight differences in structure to accomplish secondary operable features.

In a fourth embodiment of the invention, the injection needle retracting mechanism is basically the same and the functional principal is identical except that instead of using the syringe 7" for injecting fluids such as intramuscular absorbing medication or intravenous pharmaceuticals, the invention is directed to removing fluid sample such as blood from the body. The usual method to accomplish this procedure is to employ a system that includes a hypodermic needle and a barrel including an interconnecting needle that pierces a vacuum container or vial drawing the sample into the container when the connection is made. The same problem exists with this system as it exposes a sharp hypodermic needle with only a removable cover for protection. The inside interconnecting needle is of little danger as it is completely surrounded by the barrel and is unaccessible to most parts of the medical practitioner's body, at least without a conscious effort.

The invention's embodiment for a device used in taking body fluid samples is illustrated in FIGS. 10-12 and consists of the same hypodermic needle 9", holder 11", coiled spring 15", spring housing 21" complete with resilient fingers 23" and hooks 25" and all of the associated elements. The syringe barrel 55" and the plunger 59" however, differ somewhat in structure but retain the basic function.

The syringe barrel 55" is cylindrical in shape and has a fully open end 125' and an opposed partially opened end 127'. The open end 125' may optionally contain a replaceable centering washer 129 that fits over the end 125' and that has a predetermined inside diameter allowing a single barrel to be used with various diameter fluid sampling receptacles. Finger retaining lips 79" are positioned away from the end 125' in this embodiment serving to assist the user in handling and manipulating the device and allowing the washer 129 to be installed on the extreme end 125'. The partially opened end 127' of the barrel contains the same tapered nose 53' and tapered inner wall 57' except a straight reduced bore section 131 is added extending the end slightly. On the inside surface of the barrel 55", near the partially opened end 127', are located a pair of circumferential snap release projections 133 that have a slightly smaller inside diameter, a radial shape, and that are positioned parallel and close to one another. These projections 133 are integrally formed with the plastic barrel 55" and function as a retainer for the operating parts described later.

The material of the barrel 55" may be opaque or translucent, however, transparent is preferred to allow the sampling vial to be viewed when it is disposed within. Additionally, a color-coded identifying ring 101" may be slid over the exterior surface of the barrel 55" and be retained by a slide fit to identify the size of the syringe system such as its needle diameter, length, etc.

A hollow syringe plunger 59" is slidably received within the barrel 55". This plunger is configured to contain a converging taper 135' on one end and a hollow linking needle 137 on the other. The plunger's tapered end 135' includes a resilient seal 139 that snaps over the plunger and becomes a closure between the plunger 59" and in the straight reduced bore section 131 creating a tight hermetic seal with sufficient resistance to maintain the seal when slid linearly in the bore.

The linking needle 137 is held within the plunger 59" through a compression fit and is parallel with the inside of the barrel 55" as shown in FIGS. 11 and 12. A needle boot 141 is disposed over the needle 137 and stretches over a barbed projection 143 integral with the plunger holding the needle 137 on the inside and providing a gripping surface for the boot. The boot 141 is formed of a thin resilient material such as flexible silicone and is sized to enclosed and protect the needle when stored.

The needle end of the plunger 59" further contains an offset extended flange 145 almost the same diameter as the inside of the barrel 55" creating a stop and centering the plunger in the barrel.

The middle portion of the plunger 59" is considerably smaller in diameter than the barrel and defines a hollow plunger sleeve 73' with a rim 67' near the tapered end 135'. This rim 67' is basically the same structure as the preferred embodiment except the outer edge is tapered sharply permitting the tip of the rim 67' to be held in place between the peripheral snap release projections 133 located inside the barrel 55". When the plunger 59" is urged toward the partially open end 125' of the barrel, the rim 67' has sufficient resiliency to overcome its captivity between the projections and snap away from the containment. A similar snap action takes place when it is originally installed.

A sampling fluid vacuum container 147, vial or "B-D VACUTAINER" as it is sometimes known in the medical field is inserted inside the open end 125' of the barrel 55". The container 147 has a resilient perforatable seal 149 on one end and is domed shaped on the other much like a test tube. The container 147 is well known in the art and widely used to receive and store body fluid samples. The container is normally fabricated of glass or transparent thermoplastic and is evacuated on the inside allowing the fluid to displace the vacuum eliminating the problem of expelling trapped air.

The spring holding means associated with and positioned on the barrel 55" is as previously described using the same hypodermic needle 9", holder 11", and coiled spring 15". The spring housing 21" is slightly different and is preferably formed in two pieces that are pressed together. The front portion 21a' interfaces with the partially open end 125' of the barrel 55" and holds part of the spring 15"; the rear portion 21b' of the housing retains the balance of the spring 15". The fingers 23" and hooks 25" are also integrally formed with the rear portion 2b'.

In operation, the container 147 is inserted loosely into the barrel 55" and the hypodermic needle 9" is inserted, usually intervenously into the patient. The container 147 is urged forward into the barrel 55" where the linking needle 137 pierces the container seal 149 and the vacuum within draws the fluid into the container. The container 149 may be removed and replaced if another sample is required however, when finished, the container is urged further into the barrel 55" toward the partially open end 127' by the practitioner thumb while grasping the lips 79" with the fingers. This compressive force overcomes the resistance of the snap release projections 133 holding the extended flange 145 allowing the plunger 59" to slide forward. The plunger converging tapered nose end 53' forcibly spreads the resilient fingers 23" of the rear portion 21b' of the housing 21" radially outward to release the holder's raised lip 13". Thus, permitting the expansive force of the coiled springs 15" to break the frangible end 65' and extend the needle 9" and holder 11" into the hollow syringe plunger 59". This triggered movement fully retracts the needle 9" into the hollow center of the plunger 59' and retains it in that position by the continual urging of the coiled spring 15" thus repositioning the needle 9" into a permanently protected and harmless location. An audible clicking sound is emitted when this action is completed and the container 147 may then be removed. Any liquid on the needle is again harmlessly retained inside the syringe 7" and disposal may be safely achieved. A color coded ring 101" as shown in FIGS. 1 and 4-6, may optionally be used in this embodiment if desired.

Figure 13:
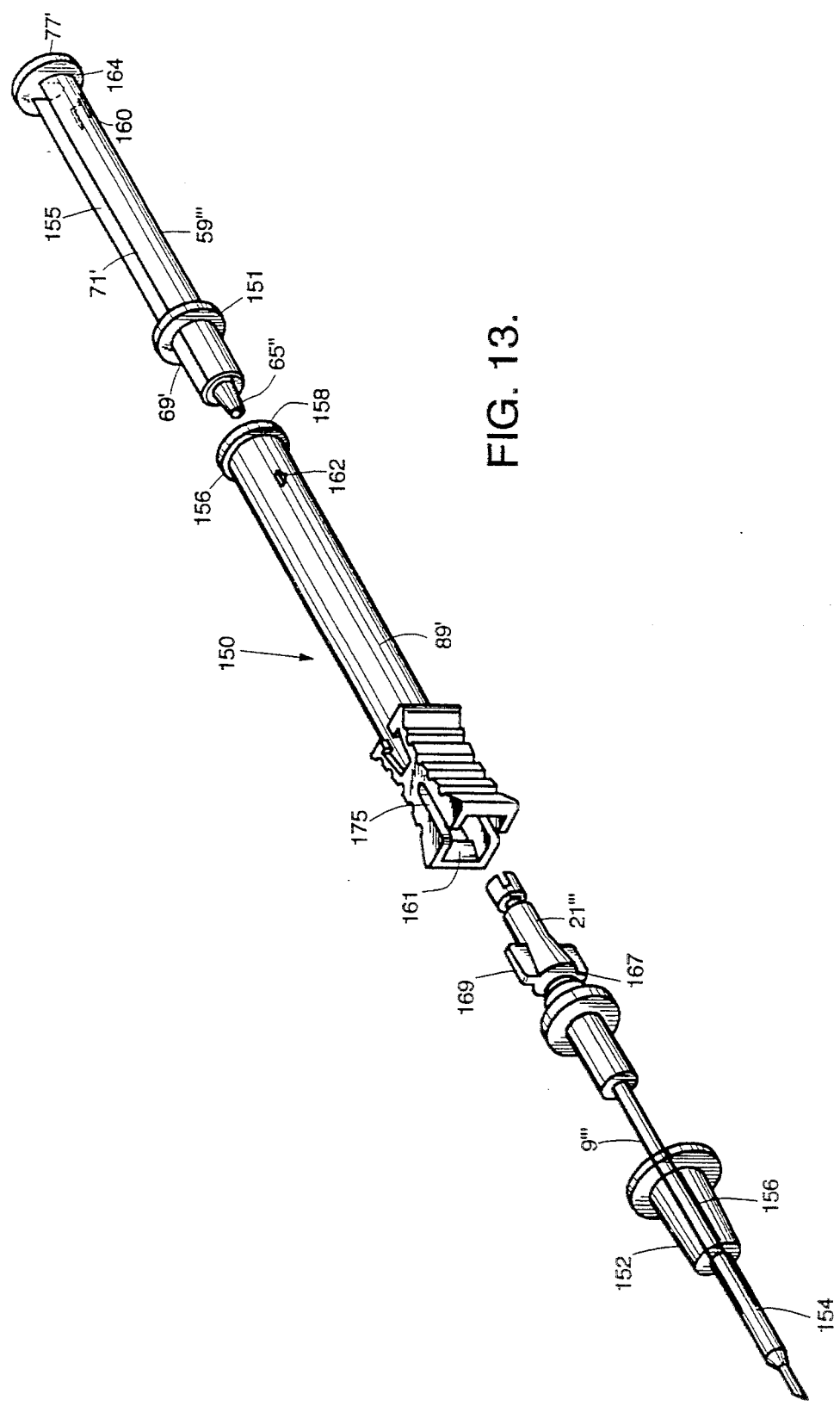
FIG. 13 is an exploded view of the intravenous catheter insertion device of the present invention.
Figure 14:
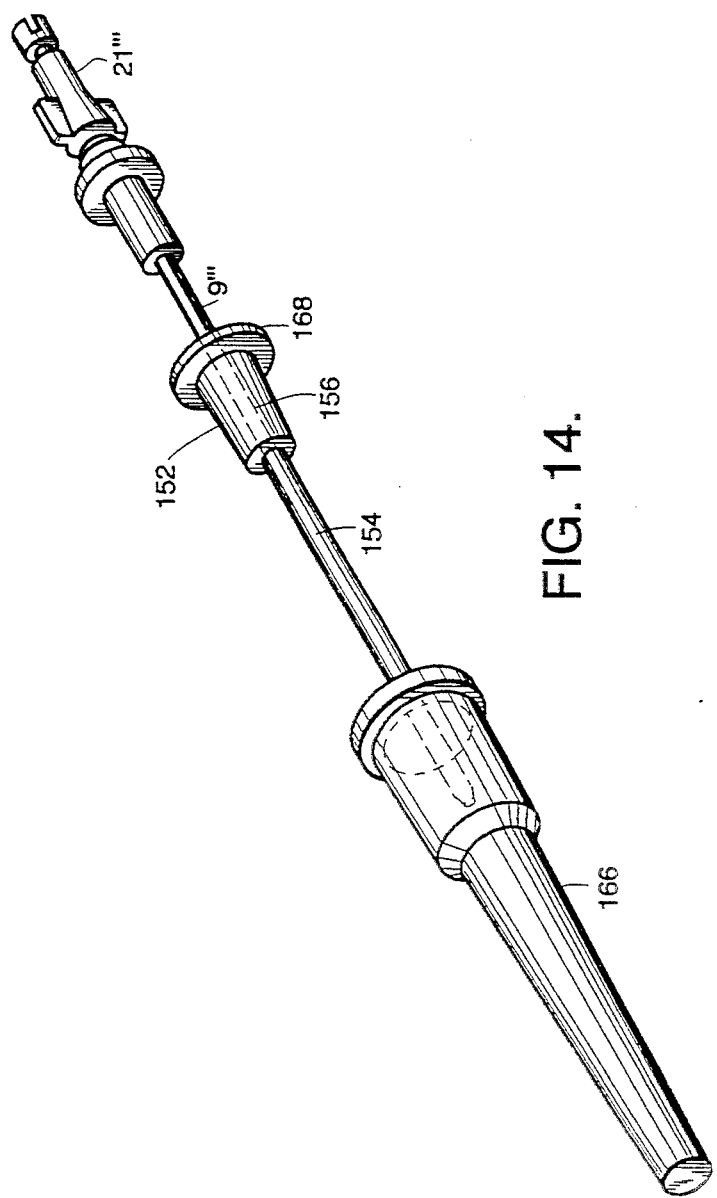
FIG. 14 is an exploded view of the intravenous catheter housing assembly of the present invention.

The fifth embodiment of the invention is an intravenous catheter insertion device illustrated in FIGS. 13-16. Referring now to FIGS. 13 and 14, the main components of the intravenous catheter insertion device 150 is a catheter hub 152 comprising a flexible catheter sleeve 154 having an interior shaft 156 with an axial passageway wherein a standard insertion needle 9'" is concentrically located. The insertion needle 9'" is mounted in a spring housing assembly 21'" which engages a barrel 55'". A plunger 59'" having an external ring portion 151 sized to be received within the barrel 55''' for sealing purposes defines a partially open or closed longitudinal cavity 71' extending therethrough, allowing a frangible end 65'' to enter the longitudinal cavity 71' of the plunger 59'''. For ease of manufacturing, the longitudinal cavity 71' may have a longitudinal slot 155 along a top side.

Between the frangible end 65'' and the longitudinal cavity 71' are outwardly tapered conical shoulders 68' having a circumferential groove 69' of a defined depth which allows the frangible end 65'' to dissociate from the outwardly tapered conical shoulders 68' as described in the preferred embodiment. The circumferential groove 69' can, of course, simply be a thinner construction of material allowing frangibility.

A pushing plate 77' is located on a posterior end 164 of the plunger 59'''. The pushing plate 77' is sized sufficient to allow the thumb or palm of a normal person to properly depress the plunger 59''' when associated with the barrel 55'''. Also, a finger retaining area 158 is associated with the posterior end 156 of the barrel 55''' so as to allow the index finger and thumb to grasp the finger retaining area 158 of the barrel 55''' as the palm presses upon the pushing plate 77'.

An extending rachet tab or tabs 160 are posteriorly located on plunger 59''' while being posteriorly flared to allow the rachet tab 160 to pass by a complementing recess or radial groove 162 defined by an interior wall 89' of the barrel 55'''. Upon full depression of the plunger 59''' within the barrel 55''', the rachet tab 160 flexibly passes by the complementing recess or radial groove 162 providing locking engagement thereby preventing the extraction of the plunger 59''' from the barrel 55'''. Also shown in FIG. 14 is a catheter needle cap 166, which engages a forwardly-positioned circumferential flange 168 of the catheter hub 152 to prevent accidental pricking by insertion needle 9''' prior to use. Optionally, the needle cap 166 can directly engage a forward portion of the spring housing assembly 21'''. In order to removably secure the needle cap 166 to the spring housing assembly 21''', an external engagement groove may be present on the forward portion of the spring housing assembly 21''' (similar to that present in the preferred embodiment.

Figure 15:
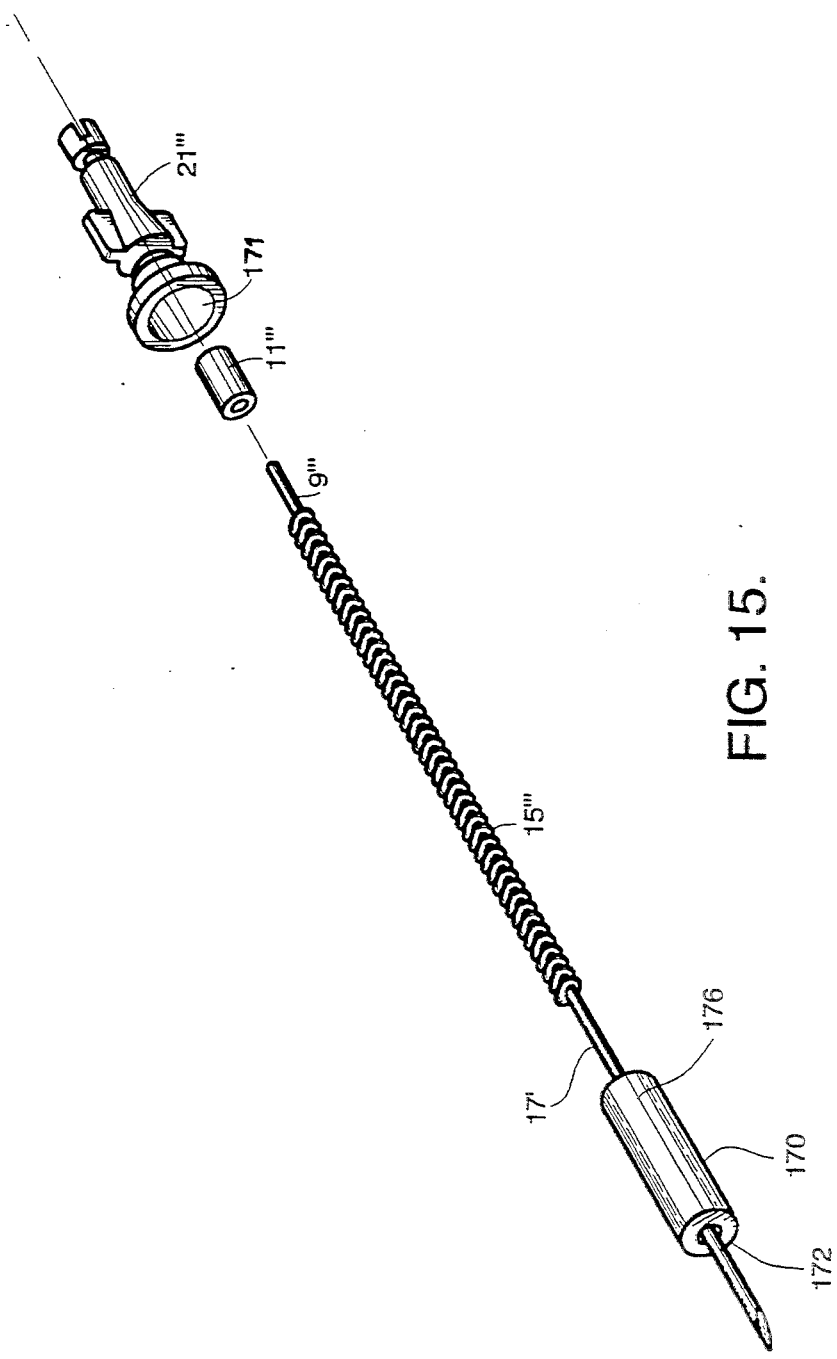
FIG. 15 is an exploded view of the spring housing assembly and insertion needle of the present invention.

As shown in FIG. 15, the needle holder 11''' is affixed to a distal end of insertion needle 9''' for placement in a first end of spring housing assembly 21'''. An opening 171 in a second end of the spring housing assembly 21''' is sized to receive a housing plug 170 having a front end aperture 172 to allow passage of the shaft 17' of the insertion needle 9''' and a circular cavity 176 having a diameter that allows the spring 15''' to be coiled when the housing plug 170 is forwardly positioned within the spring housing assembly 21'''.

Figure 16:
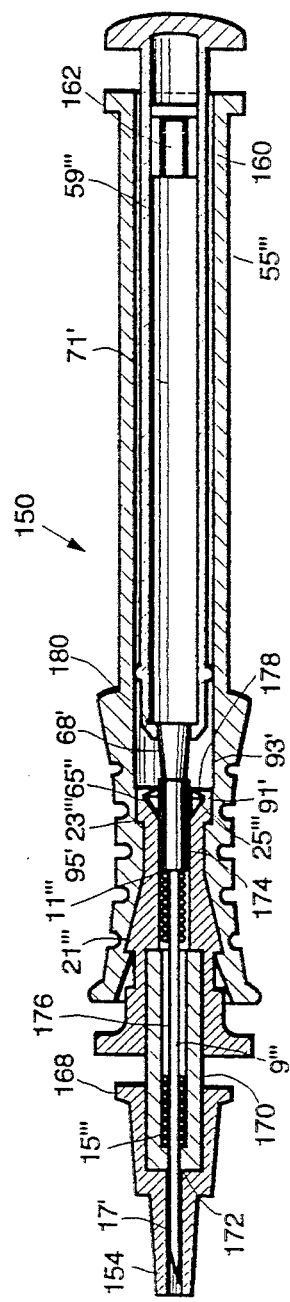
FIG. 16 is a cross-sectional view of the intravenous catheter insertion device in the present invention shown with the plunger in a partially depressed position within the barrel.

As shown in FIG. 16, the needle holder 11''' is retained by resilient fingers 23''' of the spring housing assembly 21''' by radially inwardly positioned hooks 25''' sized to engage and hold the end of needle holder 11'''. The spring 15''' is positioned axially within the cylindrical spring housing assembly 21''' and concentrically located around insertion needle 9'''. The housing plug 170 compresses the spring 15''' within spring housing assembly 21''' with the shaft 17' of insertion needle 9''' passing through a central opening 172 of housing plug 170. The housing plug 170 is permanently affixed to spring housing assembly 21''' by sonic welding, bonding, lure lock or other techniques known in the art. The coiled spring 15''' is now positioned axially within spring housing assembly 21''' between the retained needle holder 11''' and affixed housing plug 170.

As shown in FIG. 13, the barrel 55''' has internal ratchet teeth 161 sized and positioned to receive an external circumferential locking groove 167 of the spring housing assembly 21''', and a transparent viewing lens 153 for the doctor or nurse to view blood, indicating that the insertion needle 9''' and catheter sleeve 154 are located properly under the skin. The spring housing assembly 21''' has external extending tabs 169 that slide into complementary longitudinal slots 175 of the barrel 55''' for insuring proper alignment of the insertion needle 9''' when the spring housing 21''' assembly is engaged with the barrel 55'''.

In operation, the intravenous catheter insertion device 150 functions very much like the hypodermic syringe 7 of the preferred embodiment. However, after injection of the insertion needle 9''' and catheter sleeve 154 below a patient's skin, the insertion needle 9''' is withdrawn when the health care provider sees blood in the viewing window 153 wherein the plunger 59''' is pressed into barrel 55''' allowing for the dissociation of the frangible end 65'' from the outwardly tapering shoulders 68' of the plunger 59''' and the radial flexing or breaking of the resilient fingers 23''' allowing release of the needle holder 11''' of the insertion needle 9'''.

As shown in FIG. 16, a circumferential space 91' exists between the resilient fingers 23''' and the inner wall 93' of the barrel 55''', allowing the resilient fingers 23''' to flex or break which releases the needle holder 11'''. The resilient fingers 23''' will only flex or break when inwardly tapered surfaces 95' of the hooks 25''' are engaged by the outwardly tapered conical shoulders 68' of plunger 59'''. As previously described and shown in the preferred embodiment, engagement takes place when the plunger 59''' is pushed through the barrel 55''' and the frangible end 65'' abuts against the end surface 174 of the needle holder 11''' which abuts against a solidly compressed spring. A normal force of less than two pounds exerted between the end surface 174 of the needle holder 11''' and the frangible end 65'' causes the frangible end 65'' to dissociate from the outwardly tapered shoulders 68' of the plunger 59'''.

When the resilient or frangible fingers 23''' flex radially outward, the hooks 25''' release the needle holder 11''' causing the compressed spring 15''' to exert an expansive force against the needle holder 11''', propelling the insertion needle 9''' along with the needle holder 11''', as well as the dissociated frangible end 65'' into the longitudinal cavity 71' of the plunger 59'''.

Similar to the other embodiments, the above operation makes a very distinctive clicking sound alerting the health care provider that the device is now safe.

Although not shown, the longitudinal cavity 71' may be evacuated by application of a sealing plug exterior to plunger 59''' so as to allow a vacuuming effect upon the dissociation of the frangible end 65'' from the outwardly tapered shoulder 68' of plunger 59'''. Furthermore, the needle holder 11''' can be a bright or fluorescent color, while the plunger 59''' and barrel 55''' can be manufactured from a transparent or translucent material so that the retracted position is readily identified in low light conditions and the insertion needle 9''' is visibly saved for further handling, transport or discard.

Additionally, although not shown, it may be envisioned that the frangible end 65'' may be replaced with the plunger 59''' defining an aperture of sufficient size to allow the needle holder 11''', insertion needle 9''', and compressed spring 15''' to be propelled into longitudinal cavity 71' when the resilient fingers 23''' flex or break when inwardly tapered surfaces 95' of the hooks 25''' are engaged by the outwardly tapered conical shoulders 68' of plunger 59''', therefore performing the same operation as described above.

Upon further depression of the plunger 59''' into the barrel 55''' the rachet tab 160 engages the rachet lip 162, preventing the plunger 59''' from being extracted from the barrel 55'''. Additionally, at the end of resilient fingers 23''' are engaging members 178 that engage grooves 180 located at the end of outwardly tapered conical shoulders 68' of plunger 59''' further preventing the plunger 59''' from being removed or extracted from barrel 55'''.

Besides the above-identified differences, the fifth embodiment of the invention functions substantially as the preferred embodiment and includes all variations described in the all of the above-described embodiments. The materials necessary for each of the components of the fifth embodiment are similar to those materials as described in the first embodiment of the invention.

It should be appreciated from the foregoing description that the present invention describes an improved hypodermic syringe and intravenous catheter insertion device with a retractable needle which is simple in construction, yet completely effective in retracting a needle once the needle has served its purpose in the injection or removal of fluids below the surface of the skin. The retractable needle system of the present invention can be conveniently assembled from a minimum number of separate parts, all of which can be manufactured with relatively inexact precision, all of which are configured to facilitate compact and efficient operation. The retractable needle system of the present invention can be fully and safely operated by the use of one hand to retract the needle and allow for safe handling, transport and discard.

Although the present invention has been described in detail with reference only to the presently-preferred embodiment, it will be appreciated by those of ordinary skill in the art that various modifications can be made without departing from the invention. Accordingly, the invention is limited only by the following claims.

What is claimed is:

1. An intravenous catheter insertion device for inserting a catheter sleeve with associated hub for providing medicinals to a patient comprising:
   (a) an insertion needle sized to be received concentrically within the catheter sleeve for insertion of said catheter sleeve along with said insertion needle below a patient's skin;
   (b) a barrel adapted to receive a plunger;
   (c) a plunger, including an interior cavity and a frangible end adjacent thereto, said plunger sized to be received within and slide through said barrel; and
   (d) a spring housing means associated with and attachable to said barrel, for holding said insertion needle and selectively retracting said insertion needle into said interior cavity of said plunger when said plunger abuts against a surface within said barrel and moves beyond a portion of said barrel, causing breakage of said frangible end, and allowing said frangible end of said plunger to separate, wherein said spring housing means comprises; a holder for holding said insertion needle; and a spring means for exerting an expansive force between an end of said holder and said spring housing means, wherein said spring housing means selectively holds said holder and said spring means therebetween, while allowing said insertion needle to extend from said spring housing means in an assembled condition, wherein said spring housing means has extending resilient finger with interior and inferiorally positioned hooks to retain said end of said holder in an assembled condition wherein said frangible end of said plunger has an engaging and complementing surface which abuts up against said hooks of said extending resilient fingers, spreading said extending resilient fingers radially outwardly to release said end of said holder against the expansive force of said spring means when said plunger moves beyond said portion of said barrel, and wherein said spring housing means is attachable to said barrel and lockable thereto, preventing removal of said spring housing means from said barrel.

2. The intravenous catheter insertion device as specified in claim 1 wherein said frangible end of said plunger separates when a predetermined normal force is exerted between said frangible end of said plunger and said holder.

3. The intravenous catheter insertion device as specified in claim 2 wherein said frangible end of said plunger spreads said extending resilient fingers radially outwardly upon depression of said plunger past a predetermined point within said barrel prior to exertion of said predetermined normal force allowing said frangible end to disassociate and said spring means to propel said holder and insertion needle into said cavity of said plunger.

4. The intravenous catheter insertion device as specified in claim 1 wherein said spring housing means operatively associates with an end of said barrel.

5. The intravenous catheter insertion device as specified in claim 4 wherein said interior cavity of said plunger is evacuated prior to the separation of said frangible end from said plunger.

6. The intravenous catheter insertion device as specified in claim 1 further comprising ratchet means for engaging said plunger within said barrel, preventing separation of said plunger from said barrel after said plunger is depressed within said barrel, a first portion of said ratchet means coupled to said plunger and a second portion of said ratchet means coupled to said barrel.

7. The intravenous catheter insertion device as specified in claim 6 wherein said spring housing means includes an external circumferential groove and wherein an end of said barrel includes a plurality of ratchet teeth, said ratchet teeth sized to receive said groove and allow secure engagement between said spring housing means when associated with said end by positioning said groove into said end of said barrel, thereby securing said spring housing means to said barrel.

8. The intravenous catheter insertion device as specified in claim 7 wherein said spring housing means includes external extending tabs and wherein said end of said barrel includes longitudinal slots sized to receive said extending tabs thereby insuring proper alignment of said insertion needle when said spring housing means is engaged with said barrel.

9. The intravenous catheter insertion device as specified in claim 8 wherein said holder is a highly visible color and wherein said plunger and said barrel are made of a translucent or transparent material to allow viewing said holder when injected to said plunger through said barrel.

10. The intravenous catheter insertion device as specified in claim 9, wherein a forward portion of said spring housing means includes an external engagement groove for engagement with a needle cap.

11. An intravenous catheter insertion device for inserting a catheter sleeve with associated hub for providing medicinals to a patient comprising:
  (a) an insertion needle sized to be received concentrically within the catheter sleeve for insertion of said catheter sleeve along with said insertion needle below a patient's skin;
  (b) a barrel adapted to receive a plunger;
  (c) a plunger, including an interior cavity, said plunger sized to be received within and slide through said barrel; and
  (d) a spring housing means associated with and attachable to said barrel, for holding said insertion needle and selectively retracting said insertion needle into said interior cavity of said plunger when said plunger abuts against a surface within said barrel and moves beyond a portion of said barrel, wherein said spring housing means comprises; a holder for holding said insertion needle; and a spring means for exerting an expansive force between an end of said holder and said spring housing means, wherein said spring housing means selectively holds said holder and said spring means therebetween, while allowing said insertion needle to extend from said spring housing means in an assembled condition, wherein said spring housing means has extending resilient fingers with interior and inferiorally positioned hooks to retain said end of said holder in an assembled condition wherein an end of said plunger has an engaging and complementing surface which abuts up against said hooks of said extending resilient fingers, spreading said extending resilient fingers radially outwardly to release said end of said holder against the expansive force of said spring means when said plunger moves beyond said portion of said barrel, and wherein said spring housing means is attachable to said barrel and lockable thereto, preventing removal of said spring housing means from said barrel.

12. The intravenous catheter insertion device as specified in claim 11 wherein said end of said plunger spreads said extending resilient fingers radially outwardly upon depression of said plunger past said predetermined point within said barrel prior to exertion of said predetermined normal force allowing said spring means to propel said holder and insertion needle into said cavity of said plunger.

13. The intravenous catheter insertion device as specified in claim 11 wherein said spring housing means operatively associates with an end of said barrel.

14. The intravenous catheter insertion device as specified in claim 11 further comprising ratchet means for engaging said plunger within said barrel, preventing separation of said plunger from said barrel after said plunger is depressed within said barrel, a first portion of said ratchet means coupled to said plunger and a second portion of said ratchet means coupled to said barrel.

15. The intravenous catheter insertion device as specified in claim 14 wherein said spring housing means includes an external circumferential groove and wherein an end of said barrel includes a plurality of ratchet teeth, said ratchet teeth sized to receive said groove and allow secure engagement between said spring housing means when associated with said end by positioning said groove into said end of said barrel, thereby securing said spring housing means to said barrel.

16. The intravenous catheter insertion device as specified in claim 15 wherein said spring housing means includes external extending tabs and wherein said end of said barrel includes longitudinal slots sized to receive said extending tabs thereby insuring proper alignment of said insertion needle when said spring housing means is engaged with said barrel.

17. The intravenous catheter insertion device as specified in claim 16 wherein said holder is a highly visible color and wherein said plunger and said barrel are made of a translucent or transparent material to allow viewing said holder when injected to said plunger through said barrel.

18. The intravenous catheter insertion device as specified in claim 17, wherein a forward portion of said spring housing means includes an external engagement groove for engagement with the needle cap.

19. A retractable needle system comprising:
  (a) barrel means for providing a fluid reservoir;
  (b) plunger means for expelling a fluid in said fluid reservoir, said plunger means defining an interior cavity and slidably and snugly fitting within said barrel means;
  (c) catheter sleeve means for providing intravenous fluid access, said catheter sleeve means having a flexible shaft adapted to receive an insertion needle having a holder end; and
  (d) spring holding means for releasably holding a spring between said spring holding means and a holder end of an insertion needle, said spring holding means having resilient fingers with interior and inferiorly positioned hooks engageable by said plunger means, said spring holding means coupled to said barrel means and releasing said spring after said plunger means reaches said spring holding means, whereby said spring urges a holder end of an insertion needle into said interior cavity.

20. An intravenous catheter insertion device comprising a captured needle received concentrically within a catheter sleeve for insertion of said catheter sleeve along with said insertion needle below a patient's skin, a spring loaded needle means for holding and ejecting sole captured needle, barrel means connectable to said spring loaded needle means on one end, and a plunger means having a hollow portion, said plunger means positionable within and movable through said barrel means, said plunger means having a breakable end adjacent said hollow portion which breaks free from one end of said plunger means and allows said captured needle to be ejected into said hollow portion of said plunger means within said barrel means, wherein said spring loaded needle means has a housing with resilient fingers on one end, which can be spread radially outward by said one end of said plunger means in contact therewith to release said captured needle from said housing, wherein said breakable end of said plunger means breaks allowing said captured needle to be propelled out of said housing and into said hollow portion of said plunger means and be retained therein, wherein said breakable end of said plunger means includes tapered shoulders which engage oppositely and complementing shoulders of said resilient fingers, allowing forward movement of said plunger means to spread said resilient fingers radially outward, said intravenous catheter insertion device further comprising an extending tab and a receiving slot associated between an exterior of said plunger means and the interior of said barrel means, said extending tab and said receiving slot oriented to lock together when said tab and said slot are brought into alignment with each other within said barrel means, thereby locking said plunger means within said barrel means.

21. An intravenous catheter insertion device as specified in claim 20 wherein said plunger means and said barrel means are substantially transparent, said captured needle having a distinctive appearance to be readily seen through said plunger means and said barrel means once ejected into said plunger means.

22. An intravenous catheter insertion device as specified in claim 21 wherein said plunger means includes an evacuated chamber to extract fluid from said spring loaded needle means upon the disassociation of said breakable end of said plunger means.

23. A retractable needle system comprising:
(a) a catheter sleeve having a flexible shaft with an axial passageway to concentrically receive an insertion needle having a rigid shaft, said rigid shaft having a sharp end and a holder defining an end;
(b) a spring housing having an exterior surface, resilient legs spreadable radially outward on a first end, said spring housing having exteriorly located attachment groove, an opening on a second end of said spring housing to receive said shaft of said insertion needle in sealing engagement while retaining said holder, said resilient legs having radially inwardly positioned hooks sized to engage and hold said end of said holder of said insertion needle when said shaft of said insertion needle is forwardly positioned within said spring housing, said hooks having inwardly tapered shoulders;
(c) a coiled spring means positioned axially within said spring housing between said holder and said second end of said spring housing, said spring means exerting a repulsive force between said holder of said insertion needle and said second end of said spring housing less than the retaining force exerted by said hooks of said resilient legs, thereby retaining said insertion needle within said spring housing against said repulsive force of said spring means;
(d) barrel means for engaging and holding said spring housing, said barrel means including a plurality of ratchet teeth and positioned within an interior of said barrel means to receive said extending groove of said spring housing in locking engagement, said interior of said barrel means shaped sufficient to engage said spring housing and allow said resilient legs to flex radially outward; and
(e) a plunger sized to be received concentrically within said barrel means, said plunger having a hollow axially located chamber therein, and having a dissociable end and outwardly tapered shoulders adjacent to said dissociable end, wherein said dissociable end dissociates from said plunger and is ejected into said chamber when said outward tapered shoulders forcible engage said inwardly tapered shoulders of said hooks of said resilient legs, spreading said resilient legs outwardly and disengaging said hooks from said end of said holder of said insertion needle, thereby allowing said dissociable end to dissociated under a predetermined normal force between said holder of said insertion needle and said dissociable end, and allowing said coiled spring means to eject said insertion needle from said spring housing into said chamber within said plunger.

24. An intravenous catheter insertion device comprising a captured needle received concentrically within a catheter sleeve for insertion of said catheter sleeve along with said insertion needle below a patient's skin, a spring loaded needle means for holding and ejecting sole captured needle, barrel means connectable to said spring loaded needle means on one end, and a plunger means having a hollow portion, said plunger means positionable within and movable through said barrel means, said plunger means having an aperture end adjacent said hollow portion of said plunger means and allows said captured needle to be ejected into said hollow portion of said plunger means within said barrel means, wherein said spring loaded needle means has a housing with resilient fingers on one end, which can be spread radially outward by said one end of said plunger means in contact therewith to release said captured needle from said housing allowing said captured needle to be propelled out of said housing through said aperture end of said plunger means and into said hollow portion of said plunger means and be retained therein, wherein said aperture end of said plunger means includes tapered shoulders which engage oppositely and complementing shoulders of said resilient fingers, allowing forward movement of said plunger means to spread said resilient fingers radially outward, said intravenous catheter insertion device further comprising an extending tab and a receiving slot associated between an exterior of said plunger means and the interior of said barrel means, said extending tab and said receiving slot oriented to lock together when said tab and said slot are brought into alignment with each other within said barrel means, thereby locking said plunger means within said barrel means.

25. An intravenous catheter insertion device as specified in claim 24 wherein said plunger means and said barrel means are substantially transparent, said captured needle having a distinctive appearance to be readily seen through said plunger means and said barrel means once ejected into said plunger means.

* * * * *